US011435291B2

(12) United States Patent
Odame-Ankrah et al.

(10) Patent No.: US 11,435,291 B2
(45) Date of Patent: Sep. 6, 2022

(54) PHOTOLYTIC CONVERTER

(71) Applicant: GLOBAL ANALYZER SYSTEMS LIMITED, Calgary (CA)

(72) Inventors: Charles Anim Odame-Ankrah, Calgary (CA); Brian Wayne Rosentreter, Calgary (CA)

(73) Assignee: Global Analyzer Systems Limited, Calgary (CA)

( * ) Notice: Subject to any disclaimer, the term of this patent is extended or adjusted under 35 U.S.C. 154(b) by 186 days.

(21) Appl. No.: 16/087,169

(22) PCT Filed: Apr. 7, 2017

(86) PCT No.: PCT/CA2017/050429
§ 371 (c)(1),
(2) Date: Sep. 21, 2018

(87) PCT Pub. No.: WO2017/173552
PCT Pub. Date: Oct. 12, 2017

(65) Prior Publication Data
US 2019/0086337 A1    Mar. 21, 2019

Related U.S. Application Data

(60) Provisional application No. 62/319,635, filed on Apr. 7, 2016.

(51) Int. Cl.
*G01N 21/76* (2006.01)
*B01J 19/12* (2006.01)
(Continued)

(52) U.S. Cl.
CPC ............ *G01N 21/76* (2013.01); *B01D 53/56* (2013.01); *B01D 53/74* (2013.01); *B01J 19/121* (2013.01);
(Continued)

(58) Field of Classification Search
CPC ...... G01N 21/76; G01N 21/05; G01N 21/631; G01N 31/005; G01N 33/0037;
(Continued)

(56) References Cited

U.S. PATENT DOCUMENTS 3,800,159 A * 3/1974 Lucas ............... B01J 19/123
422/186.3
3,840,342 A 10/1974 Neti et al.
(Continued)

FOREIGN PATENT DOCUMENTS

CN     1720443 A    1/2006
CN   101104954 A    1/2008
(Continued)

OTHER PUBLICATIONS

Del Negro, L. A., et al., Comparison of modeled and observed values of NO2 and JNO2 during the Photochemistry of Ozone Loss in the Arctic Region in Summer (POLARIS) mission, Journal of Geophysical Research, vol. 104, 26, 687-703, 1999.
(Continued)

*Primary Examiner* — Xiuyu Tai
(74) *Attorney, Agent, or Firm* — Young Basile Hanlon & MacFarlane, P.C.

(57) ABSTRACT

The present invention provides a photolytic converter for converting reactant molecules in a fluid sample into product molecules by photolytic dissociation with electromagnetic radiation. The converter has a reaction chamber in communication with one or more electromagnetic radiation sources, an inflow conduit for conveying the fluid sample into the reaction chamber, and an outflow conduit for conveying the fluid sample out of the reaction chamber into a receptacle, wherein at least one of the first and outflow conduits extends into the reaction chamber. The receptacle can comprise detection means for generating a signal indicative of a
(Continued)

concentration of product molecules in the processed fluid sample.

24 Claims, 15 Drawing Sheets

(51) Int. Cl.
| | |
|---|---|
| *B01D 53/56* | (2006.01) |
| *B01D 53/74* | (2006.01) |
| *G01N 21/05* | (2006.01) |
| *G01N 21/63* | (2006.01) |
| *G01N 31/00* | (2006.01) |
| *G01N 33/00* | (2006.01) |
| *G01N 31/10* | (2006.01) |

(52) U.S. Cl.
CPC .......... *B01J 19/123* (2013.01); *B01J 19/127* (2013.01); *G01N 21/05* (2013.01); *G01N 21/631* (2013.01); *G01N 31/005* (2013.01); *G01N 33/0037* (2013.01); *B01J 2219/0875* (2013.01); *G01N 31/10* (2013.01)

(58) Field of Classification Search
CPC .......... G01N 31/10; G01N 2021/0325; B01D 53/56; B01D 53/74; B01J 19/121; B01J 19/123; B01J 19/127; B01J 2219/0875; Y02A 50/245; Y02A 50/20
See application file for complete search history.

(56) References Cited

U.S. PATENT DOCUMENTS

| | | | |
|---|---|---|---|
| 5,906,946 | A | 5/1999 | Sausa et al. |
| 6,051,436 | A | 4/2000 | Reagen et al. |
| 6,346,419 | B1 | 2/2002 | Ryerson et al. |
| 7,238,328 | B2 | 7/2007 | Buhr |
| 2002/0137227 | A1 | 9/2002 | Weckstrom |
| 2002/0137228 | A1 | 9/2002 | Weckstrom |
| 2004/0108197 | A1 | 6/2004 | Buhr |
| 2004/0171846 | A1 | 9/2004 | Corrie et al. |
| 2007/0253871 | A1 | 11/2007 | Buhr |
| 2008/0165363 | A1 | 7/2008 | Gusev |
| 2008/0179178 | A1 | 7/2008 | Cabello et al. |

FOREIGN PATENT DOCUMENTS

| | | |
|---|---|---|
| CN | 100588759 C | 2/2010 |
| CN | 102449473 A | 5/2012 |
| CN | 101365654 B | 9/2012 |
| CN | 102445415 B | 7/2013 |
| CN | 104071934 A | 10/2014 |
| EP | 1567849 A1 | 8/2005 |
| EP | 1377548 B1 | 2/2009 |
| JP | H09 145622 A | 6/1997 |
| JP | H10 45401 A | 2/1998 |
| JP | 1543186 B1 | 9/2010 |
| JP | 2010237192 A | 10/2010 |
| WO | 2011/160186 A1 | 12/2011 |
| WO | 2017/173552 A1 | 10/2017 |

OTHER PUBLICATIONS

Demore, W. B., et al., Chemical Kinetics and Photochemical Data for use in Stratospheric Modeling, NASA Jet Propulsion Laboratory, Pasadena, Calif., 1997.
Fehsenfeld, F. C., et al., Ground-based intercomparison of nitric acid measurement techniques, Journal of Geophysical Research, vol. 103, 3343-3353, 1998.
Fehsenfeld, F. C., et al., Intercomparison of NO2 measurement techniques, Journal of Geophysical Research, vol. 95, 3579-3597, 1990.
Kley, D. et al., Chemiluminescence detector for NO and NO2, Atmospheric Technology, No. 12, 63-69, 1980.
Mihelcic, D., et al., An improved method of measuring tropospheric NO2 and RO2 by matrix isolation and electron spin resonance, Journal of Atmospheric Chemistry, 3, 341-361, 1985.
Ryerson, et al., An efficient photolysis system for fast-response NO2 measurements, Journal of Geophysical Research, vol. 105, 26,447-26,461, 2000.
International Search Report dated Aug. 30, 2017 (for corresponding WO 2017/173552).
Written Opinion dated Aug. 30, 2017 (for corresponding WO 2017/173552).
Extended European Search Report dated Aug. 22, 2019 (for corresponding EP17778525.0).
Office Action dated Aug. 14, 2020 from corresponding Australian Application No. 2017245952.
Office Action dated Jul. 1, 2020 from corresponding Chinese Application No. 201780034858.1.
Chinese Office Action for Application No. 201780034858.1, dated Jan. 15, 2021.
Indian Office Action for Application No. 201817041465, dated Oct. 28, 2020.
Australian Office Action for Application No. 2017245952, dated Apr. 21, 2021.
Chinese Decision of Rejection for Application No. 201780034858.1, dated Jun. 3, 2021, with Eng Translation.
Chinese Office Action for Application No. 201780034858.1, dated Dec. 1, 2021.
European Office Action for Application No. 17778525.0, dated Mar. 14, 2022.

* cited by examiner

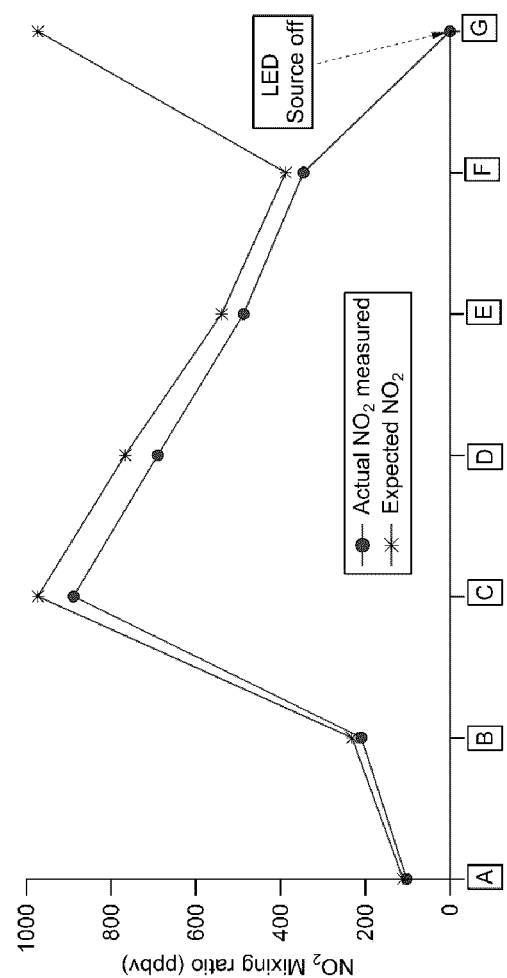
Figure 9: Results of varying concentrations of $NO_2$ (steps A-G) using the data from both the photolytic converter (Actual $NO_2$) and the molybdenum converter (Expected $NO_2$).

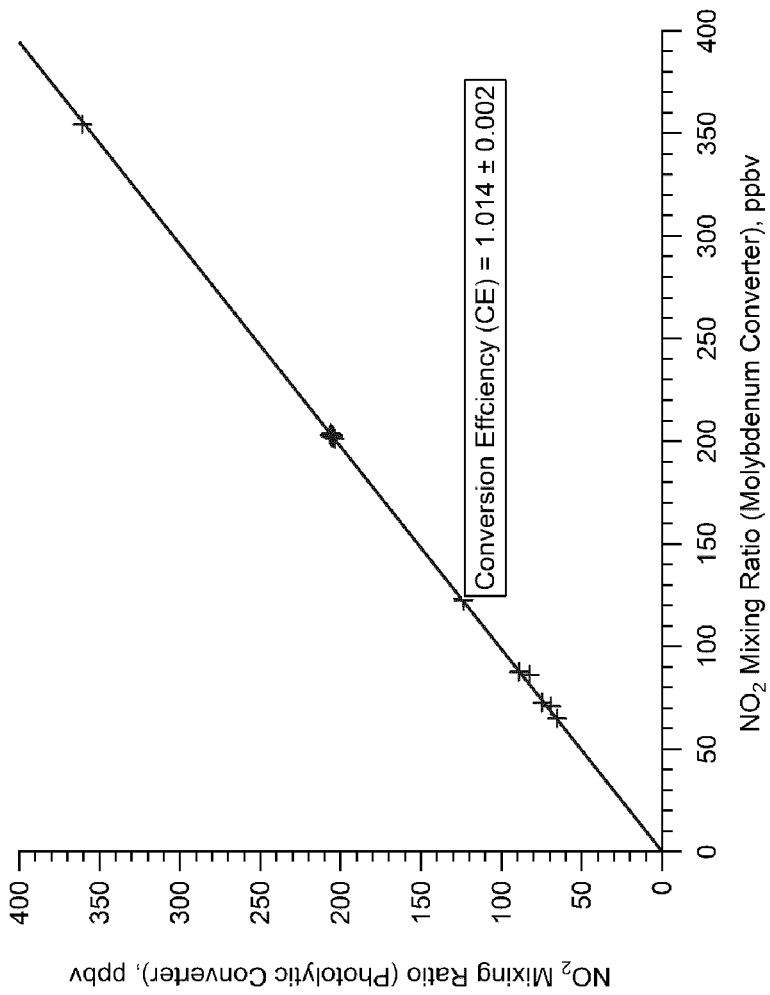
Figure 10a: NO₂ conversion in a laboratory setting using the photolytic converter device coupled with a Thermo 42i analyzer, and compared to a Thermo 42C analyzer using a molybdenum converter during a side-by-side experiment using diluted NO₂ gas from a certified 37.3ppm bottle.

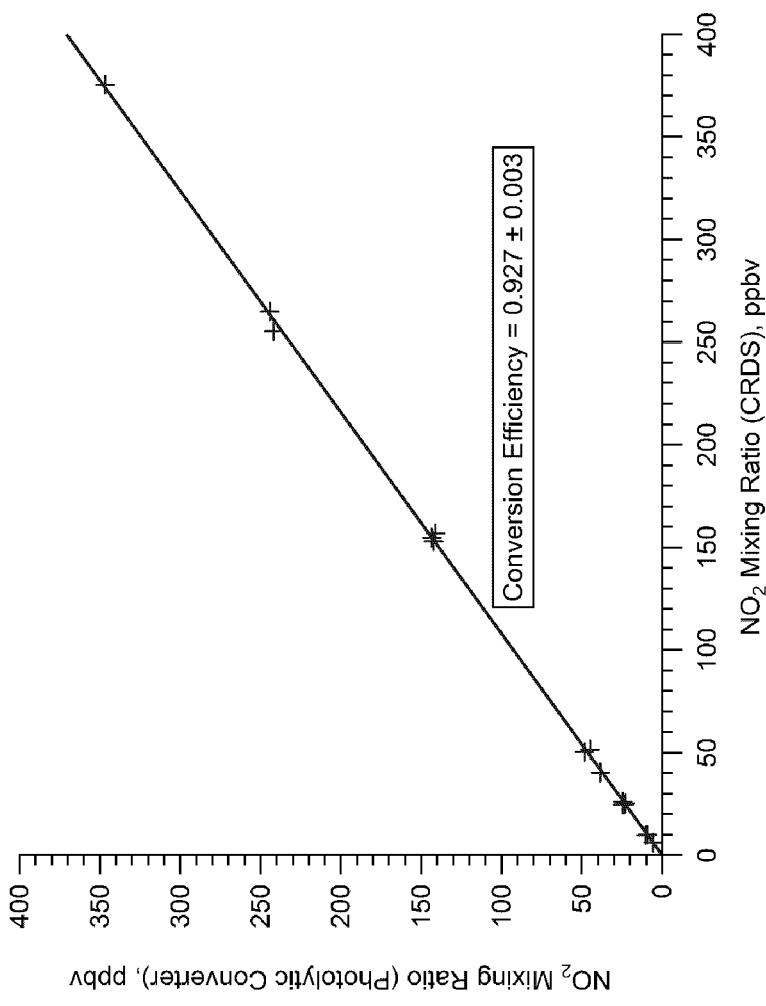
Figure 10b: Comparison of measured NO$_2$ concentrations using the pre-production Photolytic Converter System integrated with a Thermo 42i compared to a a laboratory grade direct NO$_2$ measurement device (CRDS).

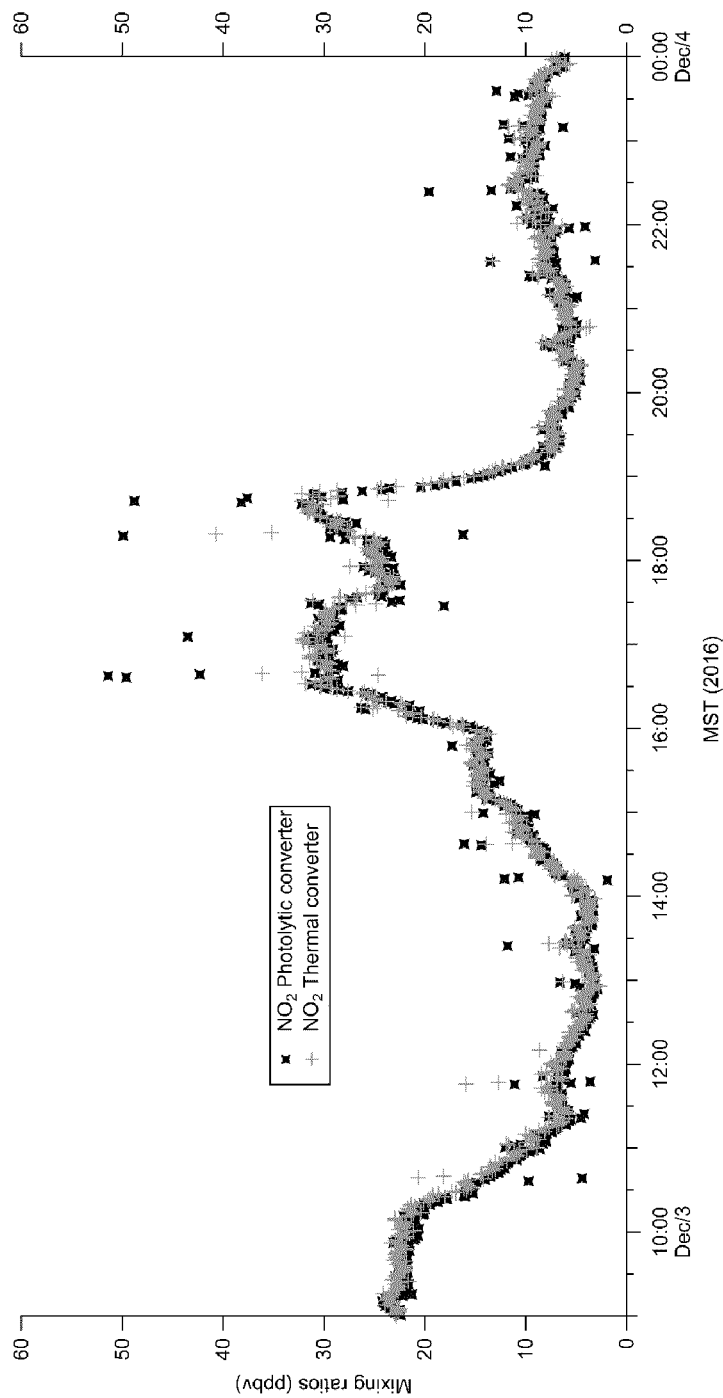
Figure 11: Data collected from a field trial with the Photolytic Converter System and a Thermo 17i with a molybdenum converter system.

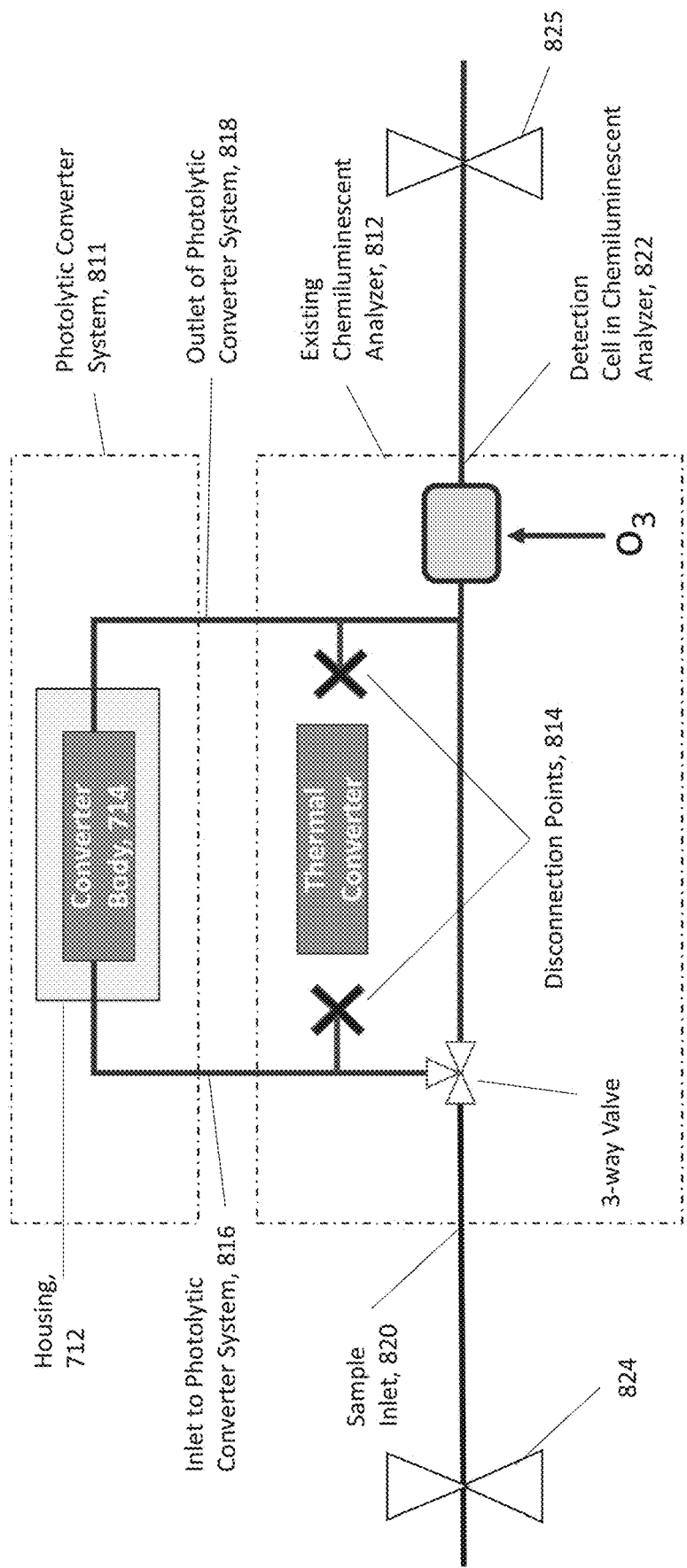
Figure 13: Example of integration of Photolytic Converter to an existing Chemiluminescent Analyzer

PHOTOLYTIC CONVERTER

FIELD OF THE INVENTION

This invention generally relates to a device and a method for indirectly measuring and/or transforming a quantity of a target molecule in a fluid sample, and more specifically relates to a photolytic converter for interference-free conversion of a reactant molecule to a desired product molecule.

BACKGROUND

Photodissociation, photolysis, or photodecomposition is a chemical reaction in which a chemical compound is broken down by photons. It is defined as the interaction of one or more photons with one target molecule. Photodissociation is not limited to visible light. Any photon with sufficient energy can affect the chemical bonds of a chemical compound. Since a photon's energy is inversely proportional to its wavelength, electromagnetic waves with the energy of visible light or higher, such as ultraviolet light, x-rays and gamma rays are usually involved in such reactions.

Two reactive forms of nitrogen oxides, namely nitrogen dioxide ($NO_2$) and nitric oxide (NO) (together known as $NO_x$) are among several toxic gases emitted by combustion sources. $NO_2$ is a classified criteria pollutant known to be a major precursor for the production of the harmful secondary pollutant ozone ($O_3$), in the troposphere.

Accurate measurements of $NO_x$ are crucial for obtaining knowledge, to combat adverse effects of the pollutants, and to meet government regulations or help policy decisions. Various methods to measure the concentration of $NO_2$ in ambient air have been developed.

In general, $NO_2$ is photodissociated at ultraviolet (UV) wavelengths below 420 nm in the following first order process, $$NO_2 + h\nu \rightarrow NO + O \quad (1)$$

with the rate constant for photolysis given by j (units of $s^{-1}$), which is the wavelength-integrated product of the photon flux (photons $cm^{-2}s^{-1}$), the weakly temperature-dependent $NO_2$ absorption cross-section ($cm^2$ $molecule^{-1}$), and the quantum yield for photodissociation (molecules $photon^{-1}$) (DeMore, W. B., et al., Chemical Kinetics and Photochemical Data for use in Stratospheric Modeling, NASA Jet Propulsion Laboratory, Pasadena, Calif., 1997).

In air, the O atom formed in reaction (1) reacts rapidly with molecular oxygen ($O_2$) to form $O_3$, $$O + O_2 \rightarrow O_3 \quad (2)$$

which can then react with NO to re-form $NO_2$, $$NO + O_3 \rightarrow NO_2^* + O_2 \quad (3)$$

where $NO_2^*$ equals electronically excited $NO_2$. The $NO_2^*$ relaxes by giving off energy as shown in formula (4) in a principle called chemiluminescence, $$NO_2^* \rightarrow NO_2 + h\nu. \quad (4)$$

Efficient conversion of $NO_2$ to NO serves to maximize that difference and improve instrumental sensitivity for $NO_2$. The light given off from Reaction (4) is used to quantify the resulting product NO.

In ambient air, a possible interference species in $NO_2$ photolysis is glyoxal $(HCO)_2$ which absorbs light in the same $NO_2$ photolysis region (350-420 nm). Glyoxal at elevated levels has a negative interference on the measured NO concentration as illustrated in the reaction equations below.

$$(HCO)_2 + h\nu \rightarrow 2HCO^\cdot \quad (5)$$

$$HCO^\cdot + O_2 \rightarrow HO_2^\cdot + CO \quad (6)$$

$$HO_2^\cdot + NO \rightarrow OH^\cdot + NO_2 \quad (7a)$$

$$RO_2^\cdot + NO \rightarrow RO^\cdot + NO_2 \quad (7b)$$

$$R-H + OH^\cdot \rightarrow R^\cdot + H_2O \quad (8)$$

$$R^\cdot + O_2 \rightarrow RO_2^\cdot \quad (9)$$

When glyoxal is present at elevated levels in the sample cell, it is photolyzed to produce formyl (HCO) radicals (eqn. 5). The HCO radicals react with molecular oxygen to form peroxyradicals, $HO_2$ (eqn. 6). The peroxyradicals, $HO_2$, or alkoxyradicals, $RO_2$, react with NO via a second order kinetic mechanism to form $NO_2$ (eqn. 7). More so, the OH radicals formed from equation 7a can initiate a second mechanism where alkyl radicals can be formed from hydrocarbons present in the sample stream. The alkyl radicals then react with molecular oxygen to generate peroxyradicals to re-activate equation 7. Although this leads to unintended reduction in the NO measurement, a well-designed photolysis chamber could minimize or prevent these side reactions from occurring (including the NO—$O_3$ recombination reactions discussed earlier). It is challenging to perfect such a system but through flow dynamics coupled with carefully selected wavelength and a novel chamber design, this can be achieved.

Conventionally, commercially available instruments used for measuring $NO_2$ in the atmosphere employ thermal catalysts for $NO_2$ conversion. These conventional devices, however, are not specific for $NO_2$. For example, one commercially available converter design is based on the reduction of $NO_2$ to NO on a heated substrate (i.e., thermal decomposition), such as molybdenum oxide, ferrous sulfate, and stainless steel. These surface-based converters are not specific for $NO_2$, as they also efficiently reduce other atmospheric nitrogen-containing compounds to a detectable form. (Fehsenfeld, F. C., et al., Intercomparison of $NO_2$ measurement techniques, Journal of Geophysical Research, 95, 3579-3597, 1990; Fehsenfeld, F. C., et al., Ground-based intercomparison of nitric acid measurement techniques, Journal of Geophysical Research, 103, 3343-3353, 1998.).

Molybdenum oxide is the most commonly used thermal substrate. Use of molybdenum converters in chemiluminescent analyzers can result in a gross overestimate of ambient $NO_2$, as it converts more than just $NO_2$ to NO. Compounds such as $NO_3$ and $N_2O_5$, Peroxyacylnitrates (PANs), alkylnitrates (ANs), and other oxidized nitrogen oxides (which are generally known as $NO_z$) can also be converted into NO when present in the sampled air mass. Because of this, the '$NO_x$' readings can and will be overestimated when these compounds are present in significant levels. The '$NO_x$' measurement read by the chemiluminescent analyzer is now a measurement of $NO_y$, which is the sum of $NO_x$ and other reactive nitrogen compounds. The resultant '$NO_x$' reading causes the chemiluminescent analyzer to overestimate $NO_2$ readings. Knowing the precise amount of $NO_2$ is important, as it determines how much ozone is being created in the troposphere which is of the utmost importance to the environmental science community.

Moreover, the Molybdenum converter is not effective in all process conditions even if the listed $NO_z$ compounds are absent, as it can also be affected by ammonia ($NH_3$), nitric acid ($HNO_3$), and water. These products deposit onto the converter's surface, preventing effective conversion (of $NO_2$ to NO) from occurring and causing uncertainty in the readings on the analyzer. Finally, the Molybdenum catalyst must be heated to 300° C.-350° C. to convert $NO_2$ to NO. The above illustrates the increased maintenance and operational costs for the analyzer, as the Molybdenum will need to be replaced more frequently.

Another technique, the photolytic dissociation of $NO_2$ with UV light followed by chemiluminescence detection of the product NO, has been employed for ambient measurements of $NO_2$ for over two decades. (Kley, D. et al., Chemiluminescence detector for NO and $NO_2$, Atmospheric Technology, 12, 63-69, 1980; Ryerson, et al., Journal Geophys. Res., 10, 2000.) This broadband photolysis technique has provided field measurement data used to evaluate and improve the current understanding of tropospheric and stratospheric ozone chemistry, radiative transfer, and sources and fate of reactive nitrogen compounds. The photolysis-chemiluminescence (P-CL) technique has been compared to other $NO_2$ measurement techniques on the ground (Mihelcic, D., et al., An improved method of measuring tropospheric $NO_2$ and $RO_2$ by matrix isolation and electron spin resonance, *Journal of Atmospheric Chemistry*, 3, 341-361, 1985; Fehsenfeld et al., 1990) and aboard aircraft (Del Negro, L. A., et al., Comparison of modeled and observed values of $NO_2$ and $J_{NO2}$ during the Photochemistry of Ozone Loss in the Arctic Region in Summer (POLARIS) mission, *Journal of Geophysical Research*, 104, 26, 687-26, 703, 1999). It has been shown to provide useful data over a wide range of concentrations and ambient environments, and has a fast start up and integration time. It also results in greater specificity for $NO_2$, but is hampered by relatively low conversion efficiency and detrimental effects of using the broadband light sources typically employed (e.g., high-pressure mercury lamp, xenon arc lamp, mercury arc lamp).

The detrimental effects are largely based on the broad spectrum of light applied to the sample. The sources that produce significant radiation in the infrared (>1000 nm) result in heat being added to the air sample, which in turn resulted in thermal conversion of labile compounds such as PANs and ANs. The broadband sources also emit radiation in the UV at both shorter and longer wavelengths than useful for $NO_2$ conversion, often resulting in photolytic conversion of interfering species (e.g., $HNO_3$ and the halogen nitrates at wavelengths less than 350 nm).

The relatively low conversion efficiency afforded by the conventional photolytic methods has typically been compensated for by allowing for longer residence time in the photolysis chamber. This practice further complicates the conversion by allowing for back reaction of the NO produced with ambient ozone. Ideally, the photolysis would take place in one second or less to minimize the effects of the back reaction.

In addition, the existing photolysis-based methods have not seen widespread use because of the operating costs associated with replacement of the relatively short-lived light sources (typically 200-1500 hours of continuous operation depending on the lamp, with costs ranging from $200-$900 per lamp). Replacing these lamps also equates to man hours spent and instrument downtime incurred, both adding costs to the testing procedure. In addition to these costs, additional costs of prior methods include the mechanical shuttering devices, filters, broadband light source power requirements and elaborate positioning devices employed to position the broadband light source.

U.S. Pat. No. 7,238,328 discloses a solid-state light source photolytic $NO_2$ converter including a reaction chamber made of a reflective material with diffuse reflective properties, whereby the reaction chamber includes a low volume gas cell wherein the gas sample residence time is less than 5 seconds is provided to avoid unwanted side reactions of $NO_2$ and NO. The converter and method described in this patent also suffer from low conversion efficiency at reduced pressures and limited range as the converter disclosed therein cannot measure higher than 2-4 ppm of $NO_2$. In addition, the converter loses conversion efficiency when operating in a reduced pressure system, making its integration into an existing analyzer even more difficult.

JP 4543186 discloses an apparatus and a chemiluminescence method for measuring nitrogen oxide concentration, wherein the apparatus is configured to have ultraviolet light source as part of the converter main body. The apparatus of this reference would also suffer with similar problems as that of U.S. Pat. No. 7,238,328, for example the reaction chamber configuration would allow for recombination reactions to occur before the NO leaves the chamber. In addition, this patent does not address the range at which they can operate, nor if the converter has a linear conversion of $NO_2$ to NO as the concentration of $NO_2$ increases.

Therefore, a need exists to provide a system and a method, which can reduce or minimize interference from photolabile species during photolytic dissociation of a reactant molecule to a product molecule, thereby improving conversion efficiency. There is also a need for a photolytic converter which can be incorporated into existing measurement systems (such as chemiluminescent analyzers) and is linear across a wide dynamic range.

SUMMARY OF THE INVENTION

Numerous other features, objects and advantages of the invention will become apparent from the following description when read in conjunction with the accompanying drawings.

In accordance with an aspect of the present invention, there is provided a photolytic converter for converting reactant molecules in a fluid sample into product molecules by photolytic dissociation with electromagnetic radiation, comprising: a converter body defining a sealed reaction chamber, and having an inner surface and an outer surface, wherein the inner surface optionally has reflective properties; one or more electromagnetic radiation sources in communication with the reaction chamber for transmitting the electromagnetic radiation into the reaction chamber for photolytically dissociating the reactant molecules in the fluid sample to form the product molecules; an inflow conduit for conveying the fluid sample into the reaction chamber, the inflow conduit having an inlet configured to be in fluid communication with a source of the fluid sample and an outlet in communication with the reaction chamber, wherein the fluid sample enters the inlet of the inflow conduit as an unprocessed fluid sample; and an outflow conduit for conveying the fluid sample out of the reaction chamber, the outflow conduit having an inlet in fluid communication with the reaction chamber and an outlet configured to be in fluid communication with a receptacle for receiving the fluid sample, wherein the fluid sample exits the outflow conduit as a processed fluid sample; wherein at least one of the inflow conduit and the outflow conduit extends into the reaction chamber.

In accordance with another aspect of the present invention, there is provided a method of photolytically converting reactant molecule present in an unprocessed fluid sample into product molecules in a processed fluid sample: providing a converted body defining a reaction chamber in communication with one or more electromagnetic sources, said converter body having: an inlet for conveying the unprocessed fluid sample into the chamber for converting the reactant molecules of the unprocessed fluid sample into the product molecules in the processed fluid sample by photolytic dissociation with electromagnetic radiation; an outlet in communication with a receptacle for conveying the processed gas sample out from the reaction chamber; passing the unprocessed fluid sample into the reaction chamber via a confined path and/or passing the processed fluid sample out of the reaction chamber via a confined path.

BRIEF DESCRIPTION OF THE DRAWINGS

FIG. 9 illustrates results of an experiment demonstrating the conversion of $NO_2$ to NO at varying concentrations of $NO_2$ using the photolytic converter of the present invention in comparison to the results to the conversion of $NO_2$ to NO with a molybdenum converter.

FIG. 10a and FIG. 10b illustrate a correlation plots of $NO_2$ measured using exemplary embodiments of the present invention vs $NO_2$ measured with know techniques in a laboratory setting. FIG. 10a shows results from initial laboratory grade testing, and FIG. 10b shows results from the pre-production prototype.

FIG. 11 illustrates results from a field trial conducted with the photolytic device integrated with a chemiluminescent analyzer and plotted against a non-modified chemiluminescent analyzer.

FIG. 13 is a schematic illustration of the integration of an embodiment of a photolytic converter in accordance with the present invention with an existing chemiluminescent analyzer, showing the disconnection points in the existing chemiluminescent analyzer and their connection to the photolytic converter System.

DETAILED DESCRIPTION

Definitions

Figure 1:
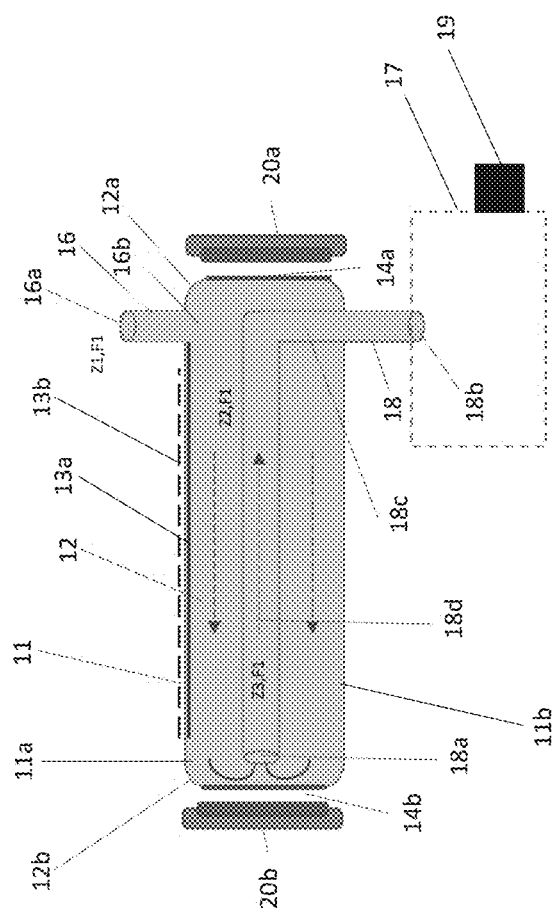
FIG. 1 illustrates a converter body in accordance with an embodiment of the photolytic converter of present invention.

Unless defined otherwise, all technical and scientific terms used herein have the same meaning as commonly understood by one of ordinary skill in the art to which this invention belongs.

As used herein, the term "electromagnetic radiation" includes radio waves, microwaves, infrared radiation, visible light, ultraviolet radiation, X-rays and gamma rays.

As used herein, the term "UV" refers to ultraviolet radiation in the region of electromagnetic spectrum including wavelengths from 40 to 4000 Å (4 to 400 nm).

As used herein, the term "chemiluminescence" refers to the emission of absorbed energy (as light) due to a chemical reaction of the components of the system. Chemiluminescence occurs in thousands of chemical reactions covering a wide variety of compounds, both organic and inorganic.

As used herein, the term "quantum yield" for a photochemical reaction refers to the number of moles of a stated reactant disappearing, or the number of moles of a stated product produced, per unit of light of the stated wavelength absorbed. Quantum yield also means the number of photon-induced reactions of a specified type per photon absorbed. Photolytic and photolysis means the use of radiant energy to produce chemical changes. Photolytic and photolysis also means decomposition of a compound into simpler units as a result of absorbing one or more quanta of radiation. Absorption cross-section means the ratio of the amount of power removed from a beam by absorption of radio energy by a target to the power in the beam incident upon the target.

As used herein, the term "solid-state light source" refers to a diode in which a semiconductor material produces either the spectrally coherent output beam (diode laser), or a narrow range of wavelengths (LED—typically full width at half maximum=5-20 nm).

As used herein, the term "fluid" refers to a substance, as a liquid or gas.

As used herein, the term "about" refers to approximately a +/−10% variation from a given value. It is to be understood that such a variation is always included in any given value provided herein, whether or not it is specifically referred to.

The present invention provides a photolytic converter for converting reactant molecules in a fluid sample into product molecules by photolytic dissociation with electromagnetic radiation.

The photolytic converter of the present invention comprises a converter body defining a reaction chamber, and having an inner surface and an outer surface, wherein the reaction chamber optionally has reflective properties. One or more electromagnetic radiation sources are placed in communication with the reaction chamber for transmitting the electromagnetic radiation into the reaction chamber for photolytically dissociating the reactant molecules in the fluid sample to form the product molecules. The photolytic converter further comprises an inflow conduit for conveying the fluid sample into the reaction chamber, and an outflow conduit for conveying the fluid sample out of the reaction chamber. The inflow conduit has an inlet in fluid communication with a source of the fluid sample and an outlet in communication with the reaction chamber, wherein the fluid sample enters the inlet of the inflow conduit as an unprocessed fluid sample. The outflow conduit has an inlet in fluid communication with the reaction chamber and an outlet in fluid communication with a receptacle for receiving the fluid sample, which exits the outflow conduit as a processed fluid sample. The photolytic converter of the present invention is designed such that at least one of the inflow and outflow conduits extends into the reaction chamber.

The conduit(s) extending to the reaction chamber can be transparent, translucent and/or opaque.

In some embodiments, the conduit(s) extending into the reaction chamber is transparent to the electromagnetic radiation for allowing the fluid sample to be irradiated by the electromagnetic radiation as it is conveyed into or out of the reaction chamber.

In some embodiments, the conduit(s) extending into the chamber is translucent or opaque.

The conduit(s) can extend in any direction within the reaction chamber.

In some embodiments, the photolytic converter of the present invention comprises one or more additional inflow conduits and/or one or more additional outflow conduits. In some embodiments, one or more the additional inflow and outflow conduits may extend into the chamber.

In some embodiments, the conduit(s) extending into the reaction chamber extend(s) in a direction parallel to, orthogonal to and/or at an angle relative to the propagation of the electromagnetic radiation within the chamber.

In some embodiments, the conduit(s) extending into the reaction chamber has a portion extending in a direction parallel to the propagation of the electromagnetic radiations within the chamber, and has a portion extending in a direction orthogonal to the propagation of the electromagnetic radiation within the chamber.

In some embodiments, the conduit(s) extending into the reaction chamber has a first portion extending in a direction parallel to the propagation of the electromagnetic radiation within the chamber, and has a second portion extending in a direction orthogonal to the propagation of the electromagnetic radiation within the chamber.

In some embodiments, the inflow and/or the outflow conduit(s) extends parallel to a longitudinal axis of the converter body. In some embodiments, the inflow and/or the outflow conduit extends parallel to a transverse axis of the converter body. In some embodiments the inflow and/or the outflow conduit(s) extends at an angle relative to the longitudinal and/or transverse axis of the converter body.

In some embodiments, the inflow and/or the outflow conduit(s) has a portion extending parallel to the longitudinal axis of the converter body and a portion extending parallel to the transverse axis of the converter body.

In some embodiments, the photolytic converter of the present invention further comprises one or more additional conduits within the reaction chamber, each having an inlet and an outlet. The additional conduits are disposed such that the outlet of an inflow conduit of the one or more additional conduits is in fluid communication with the inlet of a next conduit of the one or more additional conduits and so on, wherein the inlet of the first additional conduit is in fluid communication with the outlet of the inflow conduit and the outlet of the last conduit of the one of more additional conduits is in fluid communication with the inlet of the outflow conduit.

In some embodiments, the photolytic converter of the present invention comprises an inflow conduit and an outflow conduit as described above, and an additional conduit placed within the reaction chamber, and having an inlet in fluid communication with the outlet of the inflow conduit, and an outlet in fluid communication with the inlet of the outflow conduit.

The conduit(s) extending into the reaction chamber has a length within the reaction chamber sufficient to provide a confined path for the flow of the fluid sample into the reaction chamber (thereby to achieve a defined flow of the fluid sample into reaction chamber) or to provide a confined path for the flow of the fluid sample out of the reaction chamber (thereby to achieve a defined flow of the processed fluid sample out of the reaction chamber). For example, the length of the inflow conduit within the reaction chamber is configured to achieve a defined flow of the fluid sample into the reaction chamber, and the length of the outflow conduit within the reaction chamber is configured to achieve a defined flow of the fluid sample out of the reaction chamber.

In one embodiment, the conduit(s) entering and/or exiting the reaction chamber influence the flow in such a way that it is controlled between the exit of the inlet conduit(s) and the entrance of the outlet conduit(s). In some embodiments, the conduit(s) extending into the reaction chamber has a length within the reaction chamber sufficient to provide a confined path for the flow of the fluid sample into the reaction chamber, and/or to provide a confined path for the flow of the fluid sample out of the reaction chamber, and to provide controlled flow between the outlet of the inflow conduit and the inlet of the outflow conduit.

Desired lengths of the conduits extending into the reaction chamber can be calculated based on calculation methods known in the art.

In some embodiments, the conduit(s) extending into the reaction chamber has a length within the reaction chamber longer than the hydrodynamic entry length of the unprocessed fluid sample and/or hydrodynamic entry length of the processed fluid sample.

In some embodiments, the length of the inflow conduit(s) and/or the outflow conduit(s) within the reaction chamber is longer than the hydrodynamic entry length of the unprocessed fluid sample.

In some embodiments, the length of the inflow conduit(s) or the outflow conduit(s) within the reaction chamber is longer than the hydrodynamic entry length of the processed fluid sample.

The hydrodynamic entry length of the unprocessed fluid sample and/or the processed fluid sample can be calculated using the Reynold numbers of the fluid, which in turn depends upon the fluid kinematic viscosity, speed of fluid flow, and diameter of the conduit.

The diameter of the conduits(s) can be selected to achieve and/or control a desired speed for fluid flow. For example, the diameter of the conduit(s) can be about 3 mm to about 15 mm depending upon the length of the conduit and the length and/or width of the reaction chamber.

In some embodiments, the length of the inflow conduit(s) and/or the outflow conduit(s) within the reaction chamber is at least 30% of the length of the reaction chamber. In some embodiments, the length of the inflow conduit(s) and/or the outflow conduit(s) within the reaction chamber is at least 40%, or at least 50%, or at least 60%, or at least 70% or at least 80% or at least 90% of the length of the reaction chamber. It would be apparent to the skilled worker that there would be some space left between the chamber end wall and the inlet and or the outlet of the extending conduits to allow for the fluids to flow into and out of the reaction chamber.

In some embodiments, the length of the inflow and/or the outflow conduit(s) within the reaction chamber is from about 30% to about 99% of the length of the reaction chamber. In some embodiments, the length of the inflow and/or the outflow conduit(s) within the reaction chamber is up to about 50% or about 45%, or about 50% or about 55% or about 60% or about 70% or about 80% or about 90% or about 99% or about 99.5%, and any range in between.

In some embodiments, the inflow conduit(s) and/or the outflow conduit(s) has a first portion extending parallel to the longitudinal axis and a second portion extending transversely within the reaction chamber. In some aspects of such embodiments, the first portion extending parallel to the longitudinal axis has a length at least 50% of the length of the reaction chamber, and the second portion extending parallel to the transverse direction has a length less than 60% of the width of the reaction chamber. In some aspects of this embodiment, the length in the longitudinal axis is at least 60%, or at least 70%, or at least 80% or at least 90% of the length of the reaction chamber, and the length in the transverse direction is less than 55%, or less than 50%, or less than 45% or less than 40%, or less than 35% or less than 30% of the width of the reaction chamber.

In some embodiments, two or more conduits extend within the reaction chamber, and the reaction chamber is provided with one or more separation members to facilitate separation of the conduits from one another. In some embodiments, the separation member is a membrane. In some embodiments, the separation member is a diaphragm with openings for allowing axial extension of the conduits within the reaction chamber, while separating conduits from one another.

The conduit(s) extending into the reaction chamber can be straight, bent at angles, curved and/or spiral.

In some embodiments, the conduit(s) extending into the chamber has a flared outlet/inlet inside of the reaction chamber. In some embodiments, the outlet of the inflow conduit(s) which extends into the reaction chamber has a flared end. In some embodiments, the inlet of the outflow conduit which extends into the reaction chamber has a flared end.

In some embodiments, the inflow or outflow conduits split into two or more conduits inside the reaction chamber. In some embodiments, the outlet of the inflow conduit(s) which extends into the reaction chamber splits into two or more ends. In some embodiments, the inlet of the outflow conduit which extends into the reaction chamber splits into two or more ends.

The one or more electromagnetic sources can be placed outside or inside the converter body.

In some embodiments, the one or more electromagnetic radiation sources are provided outside the converter body, and the converter body is provided with one or more corresponding communication regions provided in the converter body, thereby allowing exposure of the radiation from the one or more electromagnetic radiation sources to the fluid sample in the reaction chamber.

In some embodiments, the one or more communication regions are provided at one end and/or one side of the converter body. In some embodiments, the one or more communication regions are provided at opposite ends and/or opposite sides of the converter body.

In some embodiments, the one or more communication regions are one or more transparent windows provided on the converter body, thereby allowing exposure of the radiation from the one or more electromagnetic radiation sources to the fluid sample in the reaction chamber.

In some embodiments, the photolytic converter of the present invention comprises a housing enclosing the converter body, and the electromagnetic radiation sources are provided in the housing and in communication with the one or more communication regions provided in the converter body. In some embodiments, the housing has structural components that hold the electromagnetic radiation sources. In some embodiments, the electromagnetic radiation sources are integrated directly into the housing.

In some embodiments, the one or more electromagnetic radiation sources are integrated in the body or are placed within the body, such that the radiation sources are in direct contact with the fluid sample. In some embodiments, the electromagnetic radiation source is located at one end and/or one side of the body. In some embodiments, the one or more electromagnetic radiation sources are located at opposite ends and/or opposite sides of the converter body.

In some embodiments, where the electromagnetic radiation source(s) are integrated with the converter body or placed within the converter body, the converter body has one or more open ends/sides to allow contact with the electromagnetic source(s) and/or an independent housing with the electromagnetic source(s) attached to it, and has an air tight seal with the electromagnetic sources and/or the independent housing, such as described in JP 4543186, incorporated herein by reference.

In some embodiments, the one or more electromagnetic radiation sources are located at two opposite ends of the converter body.

In some embodiments, the electromagnetic radiation sources are located around the outside of the converter body. In embodiments where the reaction chamber is cylindrical, the electromagnetic radiation sources may be located circumferentially around the converter body.

In some embodiments, the outlet of the inflow conduit and/or the inlet of the outflow conduit is disposed in close proximity to the portion of the reaction chamber, which is in communication with the one or more electromagnetic radiation sources. In some embodiments, the outlet of the inflow conduit and/or the inlet of the outflow conduit is adjacent the portion of the reaction chamber, which is in communication with the one or more electromagnetic radiation sources.

The converter body can be made of any material. The material can be reflective, transparent, translucent and/or opaque to electromagnetic radiation.

The converter body can be created through means of forming the material into the desired converter shape (e.g. welding, glass blowing, machining, carving, extruding), or hollowing/carving out the converter shape from a solid piece of material.

In some embodiments, the converter body is made from a solid piece of material (metal, plastic, glass, etc.). The space inside of the chamber becomes the space created from the act of hollowing out the piece of material. In some embodiments, the metal is aluminum, and/or steel.

In some embodiments, the converter body is made of glass (e.g. quartz, borosilicate, etc.). In some embodiments the converter body is made of metal (e.g. aluminum, steel, stainless steel, etc.).

The reflective properties of the reaction chamber can be derived from the material the converter body is made of, and/or by covering and/or coating the inner surface and/or the outer surface of the converter body with a material having reflective properties and/or electromagnetic radiation reflective properties.

In some embodiments, the converter body is made of electromagnetic radiation reflective material. In such cases the inner surface and/or the outer surface of the converter body has reflective properties. In some embodiments, the convert body is made of material transparent to electromagnetic radiation. In such cases the inner and/or the outer surface of the converter body can be covered or coated with a material having reflective properties and/or electromagnetic radiation reflective properties, which could be specular and/or diffuse reflective properties. In some embodiments, the converter body can be made of a material translucent and/or opaque to electromagnetic radiation. In such cases the inner surface of the converter body can be covered or coated with a material having reflective properties.

In some embodiments, the inner surface and/or outer surface of the converter body is coated with a reflective coating having specular or diffusive reflector properties.

In some embodiments, the inner surface and/or outer surface of the converter body is coated with a reflective coating comprising material having specular reflector properties, such as Krylon® mirror glass spray, Rust-Oleum Specialty® mirror effect spray, and/or thin film UV elliptical coatings In some embodiments, the inner surface and/or outer surface of the converter body is coated with a reflective coating comprising material having diffuse reflector properties, such as Teflon™ or barium sulfate ($BaSO_4$). Teflon™ means polytetrafluoroethylene (PTFE) fluorocarbon polymers available as molding and extrusion powders, aqueous dispersion, film, finishes, and multifilament yarn or fiber, and/or thin film UV diffuse reflective coatings.

In some embodiments the inner surface and/or outer surface and/or of the converter body is covered with a material having reflective properties, such as aluminum foil.

In some embodiments the converter body is made of glass, which is covered or coated with a reflective material, while leaving certain portions uncovered or uncoated to provide one more transparent windows to allow transmission of electromagnetic radiations. In some embodiments the converter body is made of quartz.

In some embodiments, the inner surface and/or outer surface of the converter body or material that is covering the converter body has specular and/or diffusive reflective properties. Specular reflector means a reflecting surface (polished metal or silvered glass) that gives a direct image of the source, with the angle of reflection equal to the angle of incidence. A specular reflector is also known as regular reflector or specular surface and it produces a direct reflection, mirror reflection or regular reflection. Diffuse reflector means any surface whose irregularities are so large compared to the wavelength of the incident radiation that the reflected rays are sent back in a multiplicity of directions.

The converter body can be elongated, square, rectangular, circular, oblong, elliptical or partially elliptical, etc.

In some embodiments, the photolytic converter of the present invention comprises an elongated body, which defines a sealed reaction chamber having a first end and a second end, an inner surface and an outer surface, and one or more windows at the first end and/or the second end, which are transparent to electromagnetic radiation. The transparent windows of the chamber are placed in communication with one or more electromagnetic sources for transmitting electromagnetic radiation into the reaction chamber. In an aspect of these embodiments, at least one of the conduits is bent or is substantially L-shaped having a first portion extending longitudinally within the reaction chamber and a second portion extending transversely within the reaction chamber. The length of the first portion is at least 60% of the length of the reaction chamber, and the length of the second portion is less than 60% of the width of the reaction chamber.

In one embodiment, only one of the inflow conduit and the outflow conduit extends into the reaction chamber. In another embodiment, both of the inflow and outflow conduits extend into the reaction chamber and each conduit has a portion extending longitudinally between the first and the second end of the reaction chamber, and a portion extending transversely with the reaction chamber.

In another embodiment, the outlet of the inflow conduit and the inlet of the outflow conduit are disposed towards opposite ends of the reaction chamber.

In another embodiment, the converter further comprises a third conduit disposed between the inflow and the outflow conduit and having an inlet in fluid communication with the outlet of the inflow conduit and an outlet in fluid communication with the outflow conduit. In some embodiments of this aspect the outlet of the inflow conduit and the outlet of the third conduit are disposed towards opposite ends of the reaction chamber.

In another embodiment, the converter body is made of glass (such as quartz), which is covered or coated with a reflective material, while leaving certain portions uncovered or uncoated to provide one more transparent windows to allow transmission of electromagnetic radiations. In some embodiments the converter body is covered with aluminum and/or aluminum foil.

The conduits of the photolytic converter of the present invention can be configured to convey the unprocessed fluid sample and the processed fluid sample into and from the reaction chamber, respectively, at a desired pressure.

In some embodiments, the inflow conduit is connected to a pressure regulator to convey the unprocessed fluid sample at a pressure lower than the pressure of the reaction chamber, and the outflow conduit is connected to a pressure regulator to convey the processed fluid sample at a pressure higher than the pressure of the reaction chamber.

In one embodiment, the inflow conduit is connected to a pressure regulator to convey the unprocessed fluid sample at a pressure higher than the pressure of the reaction chamber, and the outflow conduit is connected to a pressure regulator to convey the processed fluid sample at a pressure lower than the pressure of the reaction chamber.

In one embodiment, the inflow conduit is connected to a pressure regulator to convey the unprocessed fluid sample at a pressure higher than the pressure of the reaction chamber and the outflow conduit is connected to a pressure regulator to convey the processed fluid sample at a pressure higher than the pressure of the reaction chamber.

In one embodiment, the inflow conduit is connected to a pressure regulator to convey the unprocessed fluid sample at a pressure lower than the pressure of the reaction chamber, and the outflow conduit is connected to a pressure regulator to convey the processed fluid sample at a pressure lower than the pressure of the reaction chamber.

In one embodiment, the reaction chamber of the converter of the present invention is able to withstand pressure in the range of 170 mmHg (abs) to 1000 mmHg (abs).

In one embodiment of the photolytic converter of the present invention, the residence time of the fluid sample in the photolytic converter can be up to 10 seconds by modifying the volume of the reaction chamber and/or the shape of the reaction chamber. In one embodiment, the resident time of up to 10 seconds is achieved by using a pressure regulator and/or a flow controller.

The photolytic converter of the present invention can be used with any electromagnetic radiation source, such as light-emitting diode (LED), LASER, xenon arc lamp, etc.

In some embodiments, the electromagnetic radiation source is configured to produce UV and near UV wavelength radiation in the range of 351-415 nm In some embodiments, the electromagnetic radiation source is a source of radio waves, microwaves, infrared radiation, visible light, ultraviolet radiation, X-rays or gamma rays.

In some embodiments, the receptacle comprises a detector member in communication with the outlet of the outflow conduit for generating a signal indicative of a concentration of product molecules(s) in the processed gas sample.

In some embodiments, the photolytic converter of the present invention is for converting $NO_2$ present in the gas sample into NO. In one embodiment, the receptacle comprises a NO detector means in communication with the reaction chamber outlet for generating a signal indicative of a concentration of NO in the processed gas sample.

In one embodiment, the conversion of the $NO_2$ to NO can be used as a zeroing scheme for existing $NO_2$ analyzers employing direct measurement technologies. This embodiment uses the converter to "remove" $NO_2$ from the sample, creating a zero background that can be used to calibrate and zero the instrument.

In some embodiments, an insulating covering is provided over the body of the photolytic converter to maintain a constant fluid sample temperature, preferably at the same measurement conditions within the measurement system.

In some embodiments, the photolytic converter is provided with one or more heat dissipating devices. Examples of such devices include heat sinks, thermoelectric cooling devices (such as Peltier coolers), fans, heat pipe systems, or water cooling systems.

In some embodiments, heat dissipating device(s) are connected or attached to the electromagnetic radiation source.

In some embodiments, wherein the converter body is housed in a housing, the housing comprises structural components to hold one or more heat dissipating devices. In some embodiments, the heat dissipation devices are integrated directly into the housing.

In some embodiments, at least one heat sink is mounted to the housing and located substantially close to the at least one electromagnetic radiation source.

In some embodiments, a heat sink and active cooling device are used in tandem.

The heat dissipation devices(s) can be attached to the housing by screws, or alternatively by other fasteners such as bolts, clamps, couplings or pins.

The heat sinks and housing can be comprised of a material with good heat transfer properties, such as aluminum.

In some embodiments, the heat dissipation device(s) is provided to maintain the electromagnetic source temperature at a temperature low enough such that the fluid sample does not thermally decompose other species in the gas sample (e.g. Peroxyacetal nitrate (PANs)), and/or low enough to extend the operational life of the electromagnetic sources based off of manufacturer recommended operating parameters, by dissipating the heat orthogonally to the heat transfer device, such as a heat sink with fan and/or water cooling, or through other means such as thermoelectrically with a Peltier cooler.

In some embodiments, there are additional cooling devices placed sufficiently close to and/or attached to the housing and/or to provide additional cooling for the converter body and/or the internals of the housing of the photolytic converter.

In some embodiments, the housing provides axial alignment of the center of the converter body, the electromagnetic light sources, and the heat dissipation device(s).

In some embodiments, the photolytic converter (with or without the housing) is placed within a chassis to provide an overall photolytic converter system.

The photolytic converter of the present invention can be configured to be used in conjunction, internally or externally, with an existing chemiluminescent analyzer.

In one embodiment, the photolytic converter of the present invention can be used as an alternative to existing thermal catalytic converters in current chemiluminescent analyzers to provide consumers with the added benefits of a photolysis converter without purchasing a new analyzer. The existing thermal converter can be disconnected, and the photolytic device can be connected in its stead to convert $NO_2$ to NO for measurement by the chemiluminescent analyzer. The converter of the present application can be provided with connection members configured to connect with the inlets and outlets of the existing thermal converter.

In accordance with another aspect of the present invention, there is provided a method of photolytically converting reactant molecule present in an unprocessed fluid sample into product molecules in a processed fluid sample: providing a converted body defining a reaction chamber in communication with one or more electromagnetic sources, said converter body having: an inlet for conveying the unprocessed fluid sample into the chamber for converting the reactant molecules of the unprocessed fluid sample into the product molecules in the processed fluid sample by photolytic dissociation with electromagnetic radiation; an outlet in communication with a receptacle for conveying the processed gas sample out from the reaction chamber; passing the unprocessed fluid sample into the reaction chamber via a confined path and/or passing the processed fluid sample out of the reaction chamber via a confined path.

The confined path can be obtained by providing the reaction chamber with one or more inflow conduits and/or one or more outflow conduits as described above, wherein at let one of said conduits extents into the reaction chamber.

To gain a better understanding of the invention described herein, the following examples are set forth. It will be understood that these examples are intended to describe illustrative embodiments of the invention and are not intended to limit the scope of the invention in any way.

EXAMPLES

FIG. 1 illustrates converter body 11 defining reaction chamber 12 having first end 12a and second end 12b. In this embodiment, UV transparent windows 14a and 14b are provided at both ends 12a and 12b, respectively, to receive the UV radiation from UV sources 20a and 20b, respectively. In this embodiment, the converter body is made of quartz, wherein the portions other than windows are covered with aluminum. The converter body further has inflow conduit 16 (having inlet 16a configured to communicate with a gas source and outlet 16b in communication with reaction chamber 12), and L-shaped outflow conduit 18 having inlet 18a in communication with reaction chamber 12 and outlet 18b configured to be in communication with a receptacle 17 for the processed gas sample. In this embodiment, outlet 16b of the inflow conduit is adjacent first window 14a. The outflow conduit 18 has a portion 18d which extends longitudinally between the two ends such that its inlet 18a is adjacent second window 14b, and has a portion 18c which extends transversely in the reaction chamber. The receptacle 17 can have a NO measuring means 19, when the converter is for converting $NO_2$ present in a fluid sample into NO. The inner surface 11a and/or the outer surface 11b of the convert body 11 can be provided with reflective coating 13a/13b.

Figure 2:
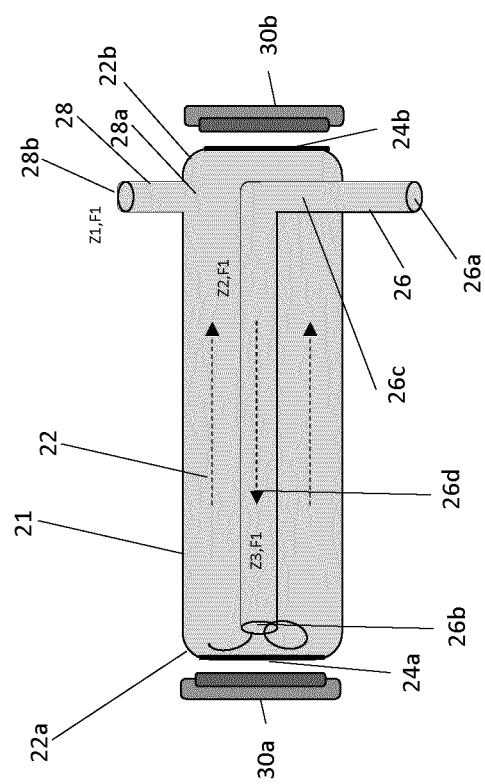
FIG. 2 illustrates a converter body in accordance with another embodiment of the photolytic converter of present invention.

FIG. 2 illustrates another embodiment of the converter body 21 defining reaction chamber 22 having first end 22a and second end 22b having UV transparent windows 24a and 24b, respectively, to receive the UV radiation from UV sources 30a and 30b respectively. In this embodiment, the inflow conduit 26 extends into the reaction chamber, and has a portion 26c which extends transversely in the reaction chamber and a portion 26d which extends longitudinally within the reaction chamber. The inlet 26a of the inflow conduit 26 is configured to communicate with a gas source and the outlet 26b is in communication with reaction chamber 22, and is in close proximity to the first window 24a. The outflow conduit 28 has inlet 28a in communication with reaction chamber 22 and outlet 28b configured to be in communication with a receptacle for the processed gas sample.

Figure 3:
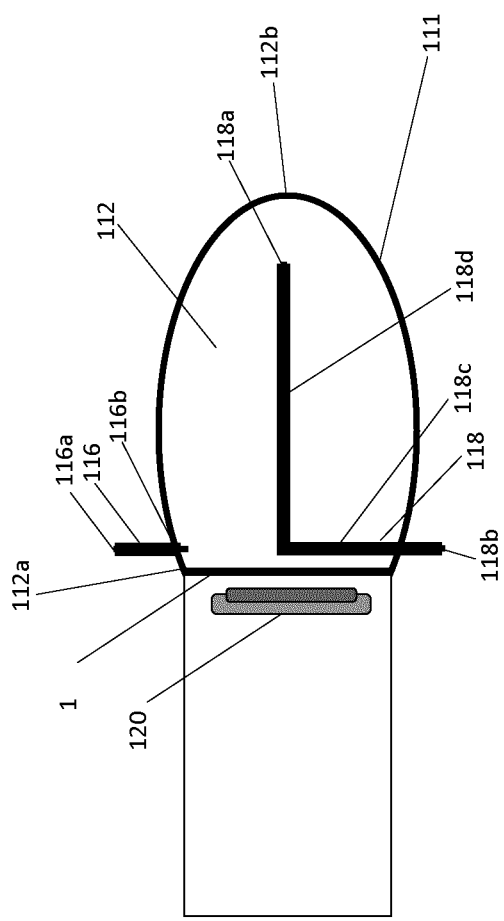
FIG. 3 illustrates a converter body in accordance with another embodiment of the photolytic converter of present invention.
Figure 4:
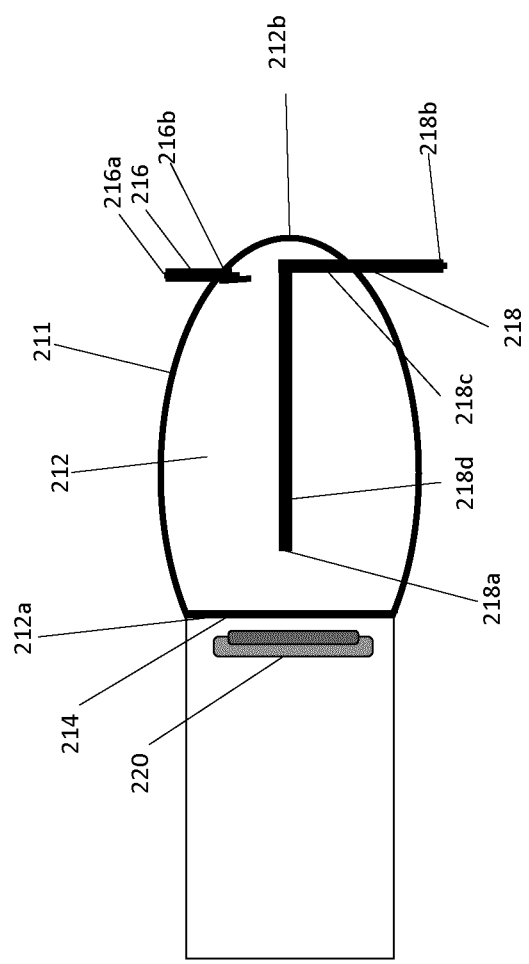
FIG. 4 illustrates a converter body in accordance with another embodiment of the photolytic converter of present invention.

FIGS. 3 and 4 illustrate a partially elliptical-shaped converter body (111 or 211), wherein the UV transparent window is provided on one end only.

In the embodiment of FIG. 3, converter body 111 has inflow conduit 116 having inlet 116a and outlet 116b, which is adjacent the UV transparent window 114 provided at end 112a to receive the UV radiation from UV source 120. The outflow conduit 118 having a portion 118c which extends transversely and a portion 118d which extends longitudinally in the reaction chamber 112 such that inlet 118a is located towards end 112b away from the window. Configuration of this embodiment can be reversed such that the conduit 118 acts as the inflow conduit to convey the fluid sample into the reaction chamber and the conduit 116 acts as the outflow conduit.

In the embodiment of FIG. 4, the converter body 211 has inflow conduit 218 having a portion 218c which extends transversely and a portion 218d which extends longitudinally in the reaction chamber 212 such that its inlet 218a is towards end 212a adjacent the UV transparent window 214 provided at end 212a, to receive the UV radiation from UV source 220. The outflow conduit 216 has inlet 216a closer to the end 212b away from the window. The configuration of this embodiment can be reversed such that the conduit 216 acts as the inflow conduit to convey the fluid sample into the reaction chamber and the conduit 218 acts as the outflow conduit.

Figure 5:
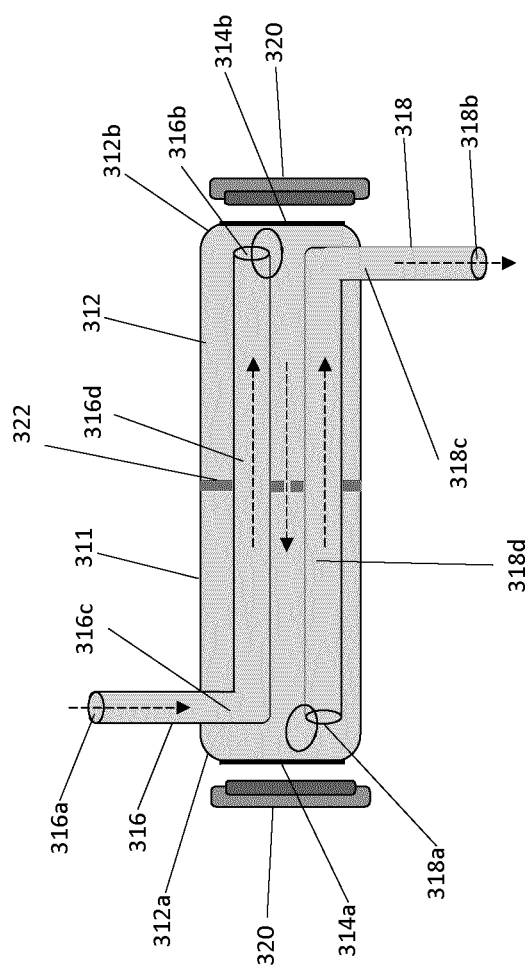
FIG. 5 illustrates a converter body accordance with another embodiment of the photolytic converter of present invention.

FIG. 5 illustrates cylindrical converter body 311 defining reaction chamber 312 having ends 312a and 312b. In this embodiment, UV transparent windows 314a and 314b are provided at opposite ends in communication with UV radiation source 320a and 320b. In this embodiment both inflow and outflow conduits 316 and 318 are L-shaped and both have a portion (316d and 318d, respectively) that extends longitudinally between the first and second ends of reaction chamber 312, such that outlet 316b of the inflow conduit is adjacent second window 314b and inlet 318a of the outflow conduit is adjacent first window 314a. Inlet 316a of the inflow conduit 316 is configured to communicate with a gas source, and outlet 318b of the outflow conduit 318 is configured to be in communication with a receptacle for the processed gas sample. In this embodiment the chamber further comprises a radial diaphragm 322 with holes to accommodate the longitudinally extension of the inflow and the outflow conduits within the reaction chamber.

Figure 6:
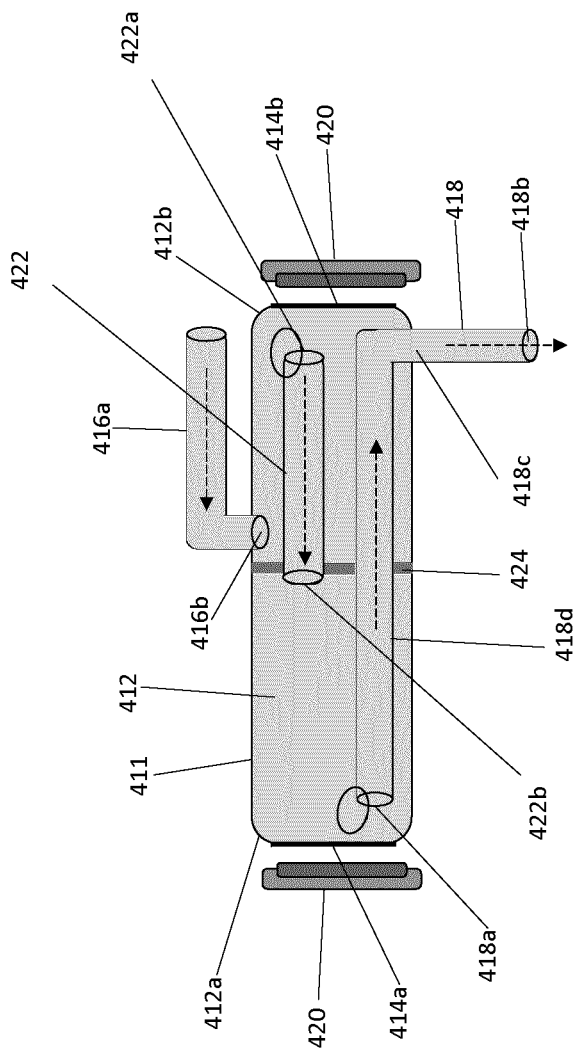
FIG. 6 illustrates a converter body in accordance with another embodiment of the photolytic converter of present invention.

FIG. 6 illustrates cylindrical converter body 411 defining reaction chamber 412 having ends 412a and 412b. In this embodiment, both ends are provided with UV transparent windows 414a and 414b, respectively. In this embodiment outflow conduit 418 has a portion 418c that extends transversely and a portion 418d that extends longitudinally between the first and second ends of reaction chamber 412, such that its inlet 418a is adjacent second window 414a The inflow conduit 416 is disposed such that its outlet 416b is relatively more towards the first window 414b. This embodiment further comprises third conduit 422 (having inlet 422a and outlet 422b), extending longitudinally between the first and second ends, and disposed between the inflow and outflow conduits, such that the outlet 416b of the inflow conduit 416 is in fluid communication with the inlet 422a, and the outlet 422b is in fluid communication with the inlet 418a of the outflow conduit to allow a flow of the gas sample from the outlet of the inflow conduit into the reaction chamber and towards the inlet of the outflow conduit, and out through the outlet of the outflow conduit. Inlet 416a of the inflow conduit 416 is configured to communicate with a gas source, and outlet 418b of the outflow conduit 418 is configured to be in communication with a receptacle for the processed gas sample. The reaction chamber further comprises a radial diaphragm 424 with holes to accommodate the axial extension of the third conduit and the outflow conduits within the reaction chamber, while separating the conduits from each other.

Figure 7:
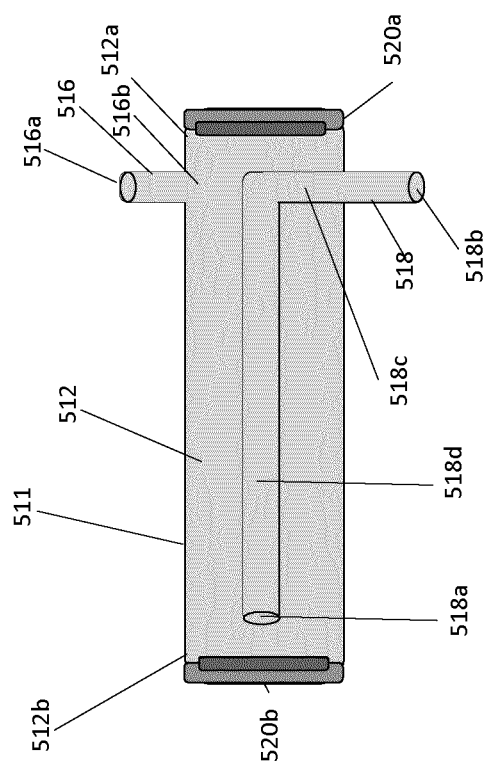
FIG. 7 illustrates a converter body in accordance with another embodiment of the photolytic converter of present invention.

FIG. 7 illustrates converter body similar to the one as described in FIG. 1, with the difference that the converter body 511 has open ends and UV sources 520a and 520b form an air-tight seal with 511 to form reaction chamber 512. The UV light sources 520a and 520b are in direct communication with the fluid sample. The converter body further has inflow conduit 516 (having inlet 516a configured to communicate with a gas source and outlet 516b in communication with reaction chamber 512) and L-shaped outflow conduit 518 (having inlet 518a in communication with reaction chamber 512 and outlet 518b configured to be in communication with a receptacle for the processed gas sample). The outflow conduit 518 has a portion 518d which extends longitudinally between the two ends and has a portion 518c which extends transversely in the reaction chamber.

Figure 8:
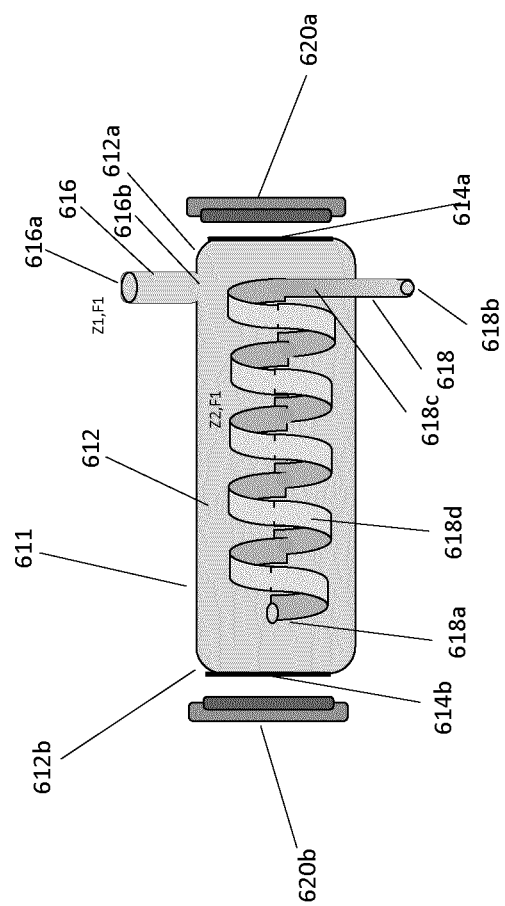
FIG. 8 illustrates a converter body in accordance with another embodiment of the photolytic converter of present invention.

FIG. 8 illustrates converter body similar to the one as described in FIG. 1, with the difference that the portion of the conduit that extends longitudinally within the reaction chamber has a spiral configuration. Specifically, the converter body 611 defines reaction chamber 612 having first end 612a and second end 612b. UV transparent windows 614a and 614b are provided at both ends 612a and 612b, respectively, to receive the UV radiation from UV sources 620a and 620b, respectively. The converter body further has inflow conduit 616 (having inlet 616a configured to communicate with a gas source and outlet 616b in communication with reaction chamber 612) and L-shaped outflow conduit 618 (having inlet 618a in communication with reaction chamber 612 and outlet 618b configured to be in communication with a receptacle for the processed gas sample). In this embodiment, outlet 616b of the inflow conduit is adjacent first window 614a. The outflow conduit 618 has a portion 618d which extends longitudinally between the two ends such that its inlet 618a is adjacent second window 614b, and has a portion 618c which extends transversely in the reaction chamber.

The Applicant has surprisingly found and established that the design of the photolytic converter of the present invention provides an efficient photolytic dissociation of target molecules in a fluid sample into product molecules. In particular, it has been established that the conversion of reactant molecules in a fluid sample (such as conversion of $NO_2$ to NO in a gas sample) can be achieved with minimal or no interferences/side reactions illustrated earlier, which results in more selective and precise measurement of reactant molecules in the fluid sample (such as $NO_2$ in a gas sample) over a wide range of operating conditions, and at pressures at or below ambient conditions (≤1 atm abs).

Without being bound by theory, it is believed that the design of the photolytic converter of the present invention provides a confined path for the movement of the fluid sample into and/or out of the reaction chamber, thereby providing an ordered flow into and out of the reaction chamber and, in some cases, within the reaction chamber itself. This ordered flow has been proven through smoke testing and fluid modeling. It is believed that the confined movement of the fluid into and/or out of the reaction chamber decreases the average velocity of the randomly moving molecules within the reaction chamber, and/or increases the effective volume of target molecules swept in unit time, which in turn reduces possibility/probability of recombination reactions between the photolysis products, along with providing uniform exposure of the fluid sample to the radiation source, thereby providing more selective and precise measurements of target molecules in a fluid sample. In addition to the ordered flow, it has been established through fluid modeling that the photolytic converter of the present invention can impart a non-turbulent whirlwind-swirling motion to the fluid as it passes through the chamber. It is believed that this non-turbulent swirling also provides order in the flow of the fluid sample and stratification of the photolyzed molecules (such that fluid exits the chamber in substantially the same order that it entered in), which again reduces the possibility/probability of recombination reactions occurring between the photolysis products.

It is also believed that, as shown in FIG. 1, when a gas sample is drawn into reaction chamber 12 through outlet 16b of inflow conduit 16 at flow rate F1, upon entry into reaction chamber 12, a pressure drop results in zone Z2, but the flowrate F1 is substantially maintained.

The sample gas is drawn towards inlet 18a of conduit 18 where another pressure change occurs in zone Z3, with similar flowrate F1. In this embodiment, the sample flow direction intersects the light path initially upon entry into reaction chamber 12 before being drawn into the same axis of propagation of the light sources. The dual stage pressure fluctuations within the reaction chamber provides the sample flow with an ordered flow pattern where the mean free path between the target/reactant molecules are greatly reduced in conduit 18, and the molecules per unit volume are greatly increased. As a result, the light flux within conduit 18 is greatly increased, resulting in efficient photolysis of the target molecules. It is also believed that due to the design of the reaction chamber, the average relative velocity of the randomly moving target/reactant molecules are decreased.

It has been observed that the residence time within conduit 18 to a detector at a sample flow of 0.7 litres per minute (lpm) is less than 1 second even at total length of 0.5 m. The implication of the novel design is that conduit 18 ensures that the effective volume of target molecules swept in unit time is increased, which significantly reduces recombination reactions between photolysis products, overcoming prior art claims that increased molecules per unit volume should have rather enhanced recombination reactions.

It has been established that a selective wavelength photolysis of $NO_2$ using the photolytic converter of the present invention can be achieved at >90% and up to 100% efficiency. The photolytic converter of the present invention can photolyze $NO_2$ from a range of 10 ppb to 37 ppm during preliminary testing. Sample data are presented here.

FIG. 9 illustrates results of an experiment demonstrating linear conversion of $NO_2$ to NO using the photolytic converter of the present invention. Experiments were conducted at 0.5-0.7 lpm, 190-250 mmHg pressure, using a Thermo Fisher Scientific (Thermo) 42C that was integrated with the photolytic converter of the present invention, and a Thermo Fisher Scientific (Thermo) 42i analyzer that was equipped with a thermal molybdenum converter. Calibrations were done using a certified 37.3 ppm $NO_2$ protocol gas from Praxair. An API dilution calibrator was used to create various mixing ratios of $NO_2$ from the 37.3 ppm certified $NO_2$ protocol gas to form concentrations of $NO_2$ from 200-1000 ppbv (shown in FIG. 9 as the Expected $NO_2$ trace, and confirmed by the use of the calibrated Thermo 42i analyzer equipped with a molybdenum catalytic thermal converter). Various mixing ratios resulting from the dilution of the 37.3 ppm certified protocol $NO_2$ gas with various ratios of zero air (a volume of air having no detectable amount of $NO_2$ or NO) is shown in FIG. 9 as stages A to G. These mixing ratios in steps A to G were sampled by both Thermo 42C and 42i analyzers. The trace in FIG. 9, "Measured $NO_2$", is the result from the Thermo 42C analyzer with the photolytic converter. During stage G, the light source was turned off, and as expected, the 42C analyzer returned to 'zero' readings on the $NO_2$ and $NO_x$ channels although 973.0 ppbv of $NO_2$ (measured by the Thermo 42i) was flowing through the photolytic converter, proving that the photolytic converter works as expected when the lights are on.

FIG. 10a and FIG. 10b illustrate correlation plots of $NO_2$ measured using exemplary embodiments of the present invention vs $NO_2$ measured with know techniques in a laboratory setting. The results shown in FIG. 10a were obtained by using a laboratory grade photolytic device coupled with a Thermo 42i analyzer, and compared to a Thermo 42C analyzer using a molybdenum converter during a side-by-side experiment using diluted $NO_2$ gas from a certified 37.3 ppm $NO_2$ bottle. The results proved that 100% photolysis can be achieved with the photolytic converter of the present invention. The results presented in FIG. 9b were obtained using a pre-production prototype with a modified mechanical design and new components (e.g. light sources, housing design) from the previous tests. This photolytic device was coupled with a Thermo 42i analyzer and compared to a laboratory grade direct $NO_2$ measurement device (CRDS). The results proved 92.7% photolysis was achieved with the pre-production model.

The pre-production prototype was then tested at a high concentration of $NO_2$ to determine its linearity. The certified $NO_2$ gas was delivered directly to the analyzer, and the results showed that the photolytic converter system converted 91.2% of the undiluted certified protocol $NO_2$ gas (37.3 ppm). These results confirm the wide linear dynamic range of the photolytic converter (within acceptable instrumental errors of ±5%), and the range of testing was limited only by the availability of a certified $NO_2$ gas.

FIG. 11 illustrates results from a field trial. The data presented is a plot showing raw $NO_2$ data from a field trial conducted with the photolytic device integrated with a Thermo 42i chemiluminescent analyzer and plotted against the $NO_2$ measured by a pre-existing Thermo 17i chemiluminescent analyzer with a thermal converter that was operating at an ambient monitoring station. There was a strong correlation between the $NO_2$ measurements obtained from each of the devices during the field trial.

Figure 12A:
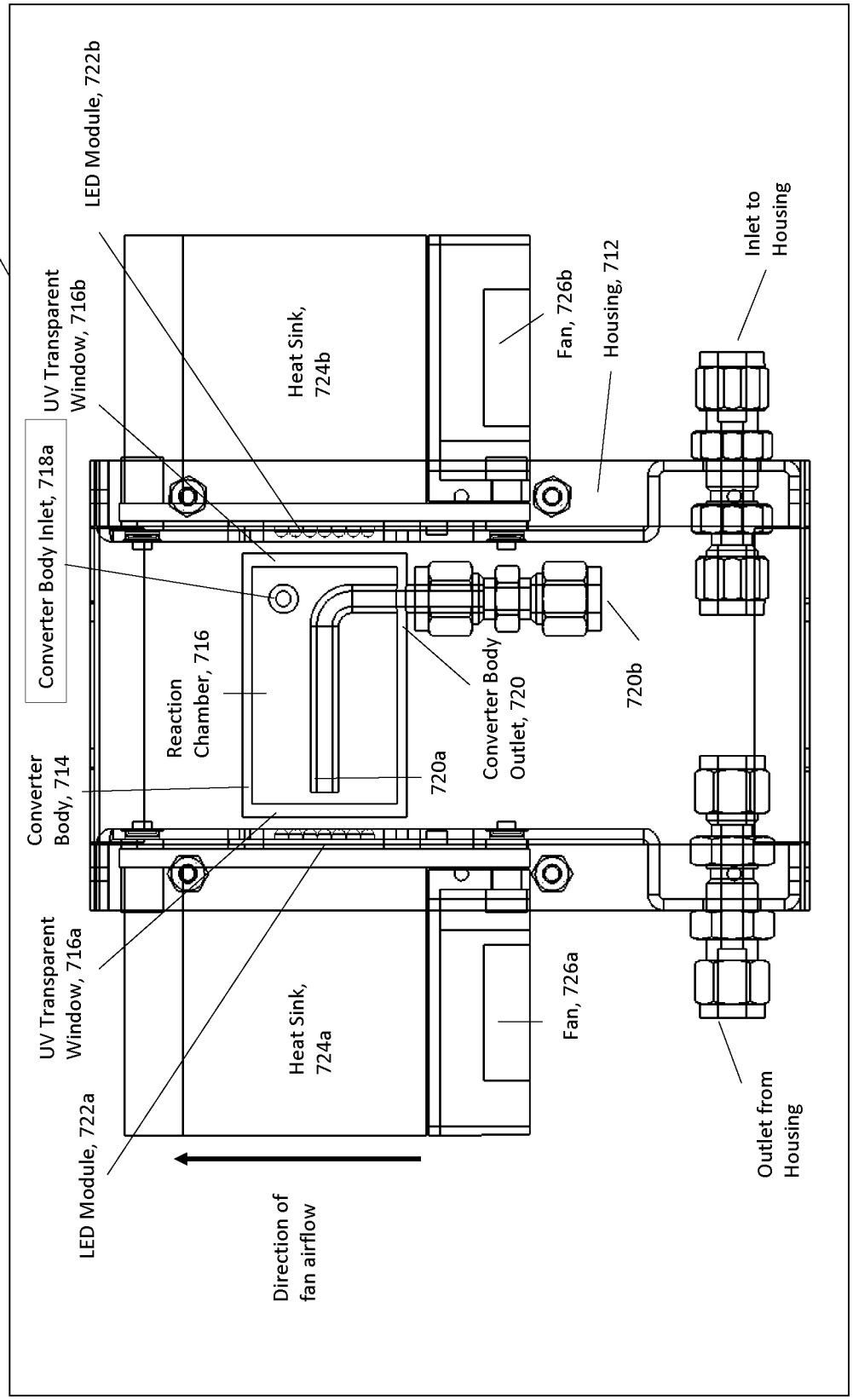
FIG. 12a is a top view of an embodiment of a photolytic converter in accordance with the present invention, comprising a converter body enclosed in a housing provided with electromagnetic radiation sources, and heat dissipation equipment attached to the housing.
Figure 12B:
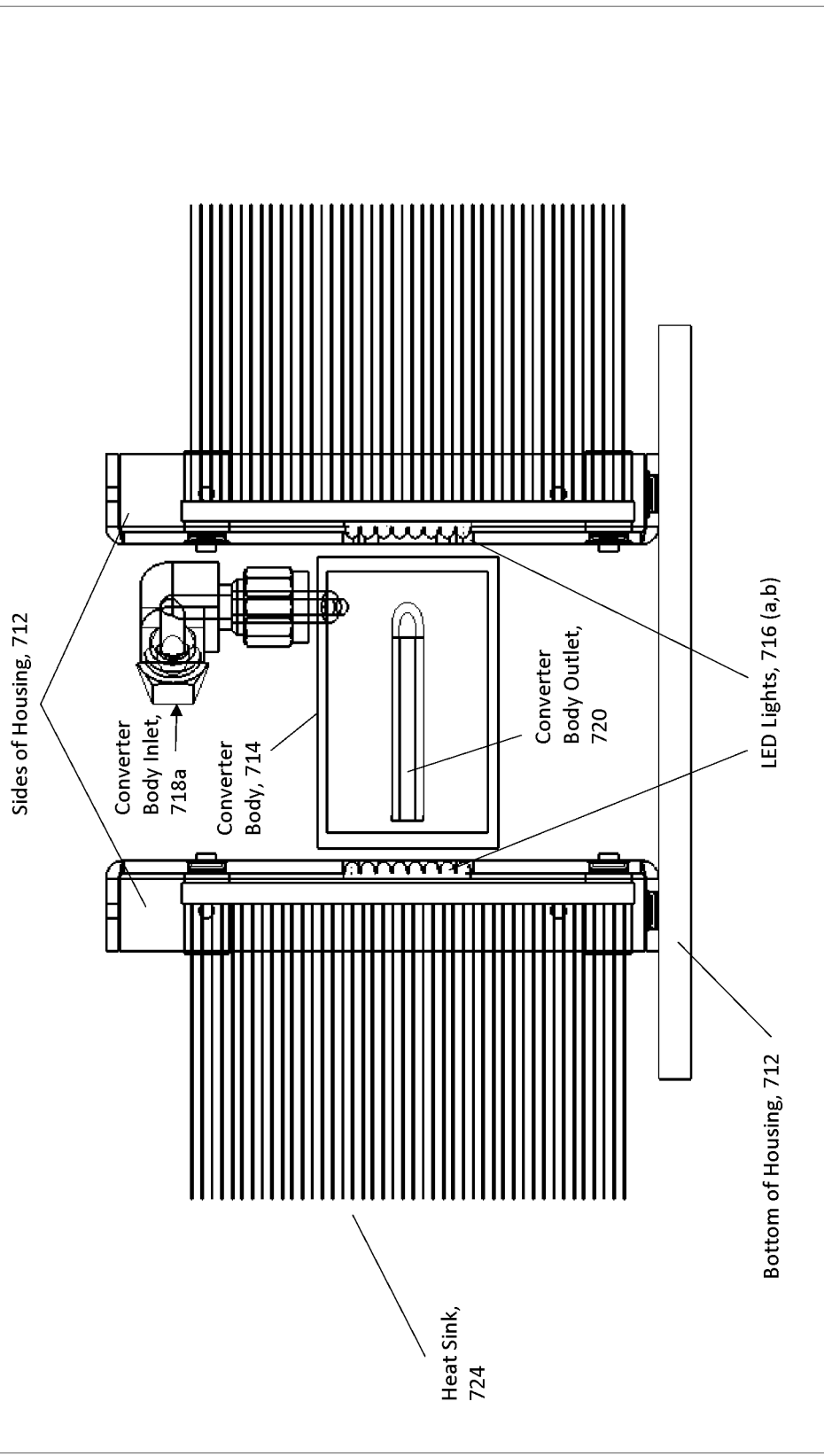
FIG. 12b illustrates a cut away view of an embodiment of the photolytic converter in accordance with the present invention, comprising a converter body enclosed in a housing, with the electromagnetic radiation source and the heat dissipation equipment attached to the housing.

FIG. 12a illustrates a top view of an embodiment of the photolytic converter placed inside a chassis 711. FIG. 12b illustrates a cut away view of the embodiment illustrated in FIG. 12a. The photolytic converter comprises a housing 712 enclosing converter body 714 defining reaction chamber 716, an inflow conduit having inlet 718a, and an outflow conduit 720 having an inlet 720a and outlet 720b. The LED modules 722a and 722b are provided inside the housing 712, such that electromagnetic radiation from the LED modules 722a and 722b are in communication with the reaction chamber. The LED modules 722a and 722b are in thermal communication with the heatsinks 724a and 724b respectively, which in turn are attached to the walls of the housing.

The housing in this embodiment is made of metal, and has cut away window portions in the housing walls wherein the LEDs are located. The reaction chamber is aligned with structural elements of the housing such that the center of the reaction chamber is in line with the center of the LEDs. The LED light passes through the windows of the reaction chamber and interacts with the sample gas flowing through the chamber. Fans 726a and 726b are integrated with the heat sinks 724a and 724b, respectively to dissipate the heat in a direction orthogonal to the LEDs such that the heat from the LEDs is not blown across the reaction chamber and/or the housing.

FIG. 13 is a schematic illustration of the integration of a photolytic converter system 811 comprising a converter body 714 and electromagnetic sources enclosed by a housing 712 and placed inside a chassis 711, with a chemiluminescent analyzer 812, showing the disconnection points 814 from the thermal converter inside of the chemiluminescent analyzer 812. The sample inlet 820 of the analyzer 812 is in fluid communication with inlet port 816 of the photolytic converter system 811, and outlet port 818 of the photolytic converter system 811 is in fluid communication with the detection cell 822 of the analyzer 812. Also shown are the pressure regulator/flow control devices 824 and 825 connected to the sample inlet 820 and detection cell 822, respectively, for controlling the flow rates of the fluid samples into and/or out of the reaction chamber.

Upon entry into the photolytic converter chassis 711, an unprocessed fluid sample (such as a gas sample comprising $NO_2$) passes through the housing 712, enters the reaction chamber 714, interacts with the LED light, and is photolyzed into a processed fluid sample (i.e. gas sample comprising NO). The processed fluid sample then exits the reaction chamber, the housing, and the photolytic converter chassis, and is passed back into the existing chemiluminescent analyzer 812. The processed fluid sample re-enters the chemiluminescent analyzer plumbing system and is transported to the detection cell 822 in analyzer 812.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

The scope of the claims should not be limited by the preferred embodiments set forth in the description, but should be given the broadest interpretation consistent with the description as a whole.

The invention claimed is:

1. A photolytic converter for converting reactant molecules in a fluid sample into product molecules by photolytic dissociation with electromagnetic radiation, the photolytic converter comprising:
a converter body defining a sealed reaction chamber, and having an inner surface and an outer surface, wherein the inner surface of the sealed reaction chamber has electromagnetic radiation reflective properties;
a housing enclosing the converter body;
one or more electromagnetic radiation sources in communication with the reaction chamber for transmitting the electromagnetic radiation into the reaction chamber for photolytically dissociating the reactant molecules in the fluid sample to form the product molecules;
an inflow conduit for conveying the fluid sample into the reaction chamber, the inflow conduit having an inlet opening configured to be in fluid communication with a source of the fluid sample and an outlet opening in communication with the reaction chamber, wherein the fluid sample enters the inlet of the inflow conduit as an unprocessed fluid sample; and
an outflow conduit for conveying the fluid sample out of the reaction chamber, the outflow conduit having an inlet opening in fluid communication with the reaction chamber and an outlet opening configured to be in fluid communication with a receptacle for receiving the fluid sample, wherein the fluid sample exits the outflow conduit as a processed fluid sample;
wherein at least one of the inflow conduit and the outflow conduit have a length so that the outlet opening of the inflow conduit and/or the inlet opening of the outflow conduit extends into the reaction chamber so that the outlet opening of the inflow conduit and/or the inlet opening of the outlet conduit extend into or through a central portion of the reaction chamber, and the length is sufficient to provide a confined path for the unprocessed fluid sample being conveyed into the reaction chamber via the inflow conduit and/or the processed fluid sample being conveyed out of the reaction chamber via the outflow conduit.

2. The photolytic converter of claim 1, wherein the inflow conduit and/or the outflow conduit extends in a direction parallel to or orthogonal to propagation of said electromagnetic radiation within said chamber, or the inflow conduit has a first portion extending in a direction parallel to the propagation of said electromagnetic radiation within said chamber and a second portion extending in a direction orthogonal to the propagation of said electromagnetic radiation within said chamber.

3. The photolytic converter of claim 1, wherein said body has a longitudinal axis and a transverse axis, wherein the inflow conduit and/or the outflow conduit has a first portion extending parallel to the longitudinal axis and a second portion extending parallel to the transverse axis.

4. The photolytic converter of claim 3, wherein the first portion has a length at least 60% of the length of the reaction chamber, and the second portion has a length less than 60% of a width of the reaction chamber.

5. The photolytic converter of claim 1, further comprising one or more additional conduits within the reaction chamber, each having an inlet and an outlet, wherein the outlet of an inflow conduit of said one or more additional conduits is in fluid communication with the inlet of a next conduit of said one or more additional conduits and so on, and wherein the inlet of a first additional conduit is in fluid communication with the outlet of the inflow conduit and the outlet of the last conduit of said one of more additional conduits is in fluid communication with the inlet of the outflow conduit.

6. The photolytic converter of claim 1, wherein the outlet of the inflow conduit and/or the inlet of the outflow conduit is adjacent the converter body, which is in communication with the one or more electromagnetic radiation sources.

7. The photolytic converter of claim 1, wherein the inner surface of the converter body has a reflective coating.

8. The photolytic converter of claim 1, wherein the outer surface of the converter body has a reflective coating or a reflective covering.

9. The photolytic converter of claim 8, wherein said reflective covering has specular and diffuse reflective properties specific to a UV light spectrum.

10. The photolytic converter of claim 1, wherein the electromagnetic source is a light-emitting diode (LED), LASER, and/or a gas discharge lamp.

11. The photolytic converter of claim 1, further comprising: a pressure regulator or flow control device for controlling a flow rate of the fluid sample into to the reaction chamber, and a pressure regulator or flow control device for controlling a flow rate of the fluid sample out of the reaction chamber, and/or a volume sized to achieve a residence time of the fluid sample in the photolytic converter up to 10s.

12. The photolytic converter of claim 1, wherein the inflow conduit and/or outflow conduit extending into and/or out of the reaction chamber respectively are transparent to the electromagnetic radiation.

13. The photolytic converter of claim 1, wherein the one or more electromagnetic radiation sources are integrated in said converter body or are placed within said converter body.

14. The photolytic converter of claim 1, wherein said one or more electromagnetic radiation sources are provided in the housing, and the converter body has one or more corresponding transparent windows, thereby allowing exposure of the radiation from said one or more electromagnetic radiation sources to the fluid sample in the reaction chamber, said housing optionally comprising a heat dissipating device.

15. The photolytic converter of claim 1, wherein the one or more electromagnetic radiation sources are in communication with said reaction chamber through said one or more windows provided at one end or one side of said converter body and/or around/circumferentially around the converter body.

16. The photolytic converter of claim 1, wherein the one or more electromagnetic radiation sources are in communication with said reaction chamber through said one or more windows provided at opposite ends and/or opposite sides of the converter body.

17. The photolytic converter of claim 1, wherein said converter body is made of metal and/or glass.

18. The photolytic converter of claim 1, wherein said converter is for converting $NO_2$ present in a fluid sample into NO, wherein the outflow conduit is configured to be in fluid communication with a receptacle having a NO detector means for generating a signal indicative of a concentration of NO in the processed fluid sample.

19. The photolytic converter of claim 1, wherein the length of the inflow conduit, the outflow conduit, or both within the reaction chamber is from about 30% to about 99.5% of the length of the reaction chamber.

20. The photolytic converter of claim 8, wherein the length of the inflow conduit and/or the outflow conduits within the reaction chamber is from about 30% to about 99.5% of the length of the reaction chamber.

21. The photolytic converter of claim 7, further comprising: a pressure regulator or flow control device for controlling a flow rate of the fluid sample into to the reaction chamber, and a pressure regulator or flow control device for controlling a flow rate of the fluid sample out of the reaction chamber, and/or a volume sized to achieve a residence time of the fluid sample in the photolytic converter up to 10s.

22. The photolytic converter of claim 6, wherein said converter body is made of metal or glass, and has transparent windows to allow exposure of the radiation from said one or more electromagnetic radiation sources to the gas sample in the reaction chamber, said housing optionally comprising a heat dissipating device.

23. The photolytic converter of claim 22, wherein said converter body is made of glass, wherein the inner surface of the converter body has a reflective coating and/or the outer surface of the converter body has a reflective coating or a reflective covering.

24. The photolytic converter of claim 7, wherein the length of the inflow conduit and/or the outflow conduits within the reaction chamber is from about 30% to about 99.5% of the length of the reaction chamber.

* * * * *